United States Patent
Durcan et al.

(12)

(10) Patent No.: US 6,383,212 B2
(45) Date of Patent: *May 7, 2002

(54) BALLOON CATHETER AND STENT DEPLOYING CATHETER SYSTEM

(75) Inventors: Jonathan P. Durcan, Temecula; Michael A. Miniati, Mountain View; Jeffrey D. Royal, San Francisco; James M. Jacobs, Mountain View, all of CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/734,071

(22) Filed: Dec. 11, 2000

Related U.S. Application Data (63) Continuation of application No. 09/282,807, filed on Mar. 31, 1999, now Pat. No. 6,200,325.

(51) Int. Cl.[7] .................................................. A61F 2/06

(52) U.S. Cl. .................... 623/1.11; 623/12.11; 606/108; 606/194; 604/101

(58) Field of Search ................................ 606/108, 194, 606/192, 195, 198; 604/96, 101, 103; 623/1.11, 12.11

(56) References Cited

U.S. PATENT DOCUMENTS

| | | | | | |
|---|---|---|---|---|---|
| 4,456,000 | A | * | 6/1984 | Schjeldahl et al. | 128/1 D |
| 5,338,298 | A | * | 8/1994 | McIntyre | 604/96 |
| 5,409,495 | A | * | 4/1995 | Osborn | 606/108 |
| 5,458,615 | A | * | 10/1995 | Klemm et al. | 606/198 |
| 5,470,313 | A | * | 11/1995 | Crocker et al. | 604/96 |
| 5,522,882 | A | * | 6/1996 | Gaterud et al. | 606/108 |
| 5,645,560 | A | * | 7/1997 | Crocker et al. | 606/192 |
| 5,749,851 | A | * | 5/1998 | Wang | 604/96 |
| 5,755,708 | A | * | 5/1998 | Segal | 604/109 |
| 5,797,878 | A | * | 8/1998 | Bleam | 604/196 |
| 5,843,116 | A | * | 12/1998 | Crocker et al. | 606/192 |
| 6,200,325 | B1 | * | 3/2001 | Durcan et al. | 606/108 |

FOREIGN PATENT DOCUMENTS

WO    WO 95/23625    * 8/1995

* cited by examiner

Primary Examiner—Pedro Philogene
(74) Attorney, Agent, or Firm—Coudert Brothers LLP (57) ABSTRACT

A balloon catheter with a balloon having first and second tapered sections adjacent the distal and proximal ends of the working length of the balloon, respectively, and third and fourth tapered sections adjacent the first and second tapered section, respectively. The first and second tapered sections taper at a first angle to a smaller outer diameter than the inflated outer diameter of the working length inflated within a deployment range of the balloon, and the third and fourth tapered sections taper at a second angle larger than the first angle. The balloon has expandable retention sections proximal and the distal to the working length of the balloon for inhibiting migration of a stent mounted on the balloon.

45 Claims, 3 Drawing Sheets

BALLOON CATHETER AND STENT DEPLOYING CATHETER SYSTEM

This is a continuation of prior application Ser. No. 09/282,807, filed Mar. 31, 1999 now U.S. Pat. No. 6,200,325.

BACKGROUND OF THE INVENTION

The invention relates to the field of intravascular balloon catheters, and more particularly to a catheter balloon having a stepped outer diameter that provides for improved dilatation and stenting.

In percutaneous transluminal coronary angioplasty (PTCA) procedures a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with liquid one or more times to a predetermined size at relatively high pressures (e.g. at least about 8 atmospheres) so that the stenosis is compressed against the arterial wall to open up the passageway. Preferably, the inflated diameter of the working length of the balloon. is approximately the same as the native diameter of the body lumen being dilated, so as to complete the dilatation but not overexpand the artery wall. However, damage to the vessel wall at and around the stenosis can result from the expansion of the balloon against the vessel wall. After the balloon is finally deflated, blood flow resumes through the dilated vessel and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Further details of stents and stent delivery systems can be found in U.S. Pat. No. 5,507,768 (Lau et al.), U.S. Pat. No. 5,458,615 (Klemm et al.), and U.S. Pat. No. 5,514,154 (Lau et al.), which are incorporated herein by reference in their entireties. Thus, stents are used to open a stenosed vessel, and strengthen the dilated area by remaining inside the vessel. Although stents have been used for some time, the effectiveness of a stent can be diminished if it is not properly implanted within the vessel. One difficulty has been deploying the stent at the desired location in the vessel and completely expanding the stent during the deployment.

Therefore, what has been needed is an improved balloon catheter with a balloon which expands to dilatate a stenosis or to deploy a stent within the patient. The present invention satisfies these and other needs.

SUMMARY OF THE INVENTION

The invention is directed to a balloon catheter with a balloon having a stepped outer diameter formed by a plurality of sections having different outer diameters, and to a stent delivery system with a stent disposed about and mounted on the balloon.

The balloon catheter of the invention generally comprises a catheter having an elongated shaft with an inflatable balloon on a distal section of the catheter shaft. The balloon may be configured for dilatation, or for stent delivery with a stent disposed about and mounted on a working length of the balloon. In one embodiment, the balloon has first and second tapered sections adjacent the distal and proximal ends of the working length of the balloon, respectively, and third and fourth tapered sections adjacent the first and second tapered section, respectively. The first and second tapered sections taper at a first angle and a second angle, respectively, to a smaller outer diameter than the inflated outer diameter of the working length inflated within a deployment range of the balloon. The third tapered section tapers at a third angle, larger than the first angle, to a smaller inflated outer diameter than the inflated outer diameter of the first tapered section inflated within the deployment pressure range of the balloon, and the fourth tapered section tapers at a fourth angle, larger than the second angle, to a smaller inflated outer diameter than the inflated outer diameter of the second tapered section inflated within the deployment pressure range of the balloon. The deployment range is the inflation pressure at which the balloon working section is intended to be expanded within the patient to expand and deploy the stent. Below the deployment range, the inflation pressure is insufficient to expand the working length of the balloon and stent thereon. Above the deployment range, the balloon may rupture as the pressure approaches the burst pressure of the balloon. The first angle and the second angle are relatively small so that the inflated outer diameter of the first and second tapered sections is not significantly less than the working length inflated outer diameter. Consequently, the first and second tapered sections can be inflated to dilatate a stenosis or expand an end of a stent which extends somewhat beyond the end of the working length of the balloon. However, the small angle of the first and second tapered sections is such that a sharp transition section on the balloon which could produce sheer forces against the vessel wall at the junction between the working length and the first tapered sections is avoided. Additionally, the length of the first and second tapered sections is relatively small, and the third and fourth tapered sections taper at a relatively large angle to a smaller outer diameter, to thereby avoid the potential damage to the vessel wall caused by the proximal and distal ends of the balloon beyond the ends of the working length expanding against the vessel wall.

In another embodiment, the balloon has expandable retention sections proximal and distal to the working length of the balloon. With a stent in place on the working length of the balloon, the retention sections inflate together at low pressure before the working section significantly expands, so that the expanded retention sections form a barrier at either end of the stent to inhibit the longitudinal displacement of the stent on the balloon. The expanded outer diameter of the retention sections, at a low pressure less than the deployment range of the balloon, is at least about 200% greater than the unexpanded outer diameter of the stent on the balloon prior to expansion of the working length of the balloon. As the inflation pressure is increased within the deployment range of the balloon, the working length of the balloon with the stent thereon will expand. The outer diameter of the retention sections is at least 30% less than the outer diameter of the working length expanded within the deployment range of the balloon, so that they form a relatively small diameter portion, which thereby minimizes potential damage to the vessel wall caused by the expansion of the proximal and distal ends of the balloon against the vessel wall.

The balloon is preferably formed of a semi or low compliant material, such as polyamides including nylon and PEBAX, and polyurethanes. The term "compliant" as used herein refers to thermosetting and thermoplastic polymers which exhibit substantial radial growth upon the application of radially expansive force. The radial growth of a balloon formed of a noncompliant material such as PET is typically less than about 0.02 mm/ATM, compared to about 0.025 to about 0.045 mm/ATM for a balloon formed of low compliant material such as nylon 12. In a presently preferred embodiment, the balloon is preformed in a mold, so that the working length, tapered sections, and retention sections of the balloon have predictable inflated outer diameters which form when the balloon is inflated within a deployment range of the balloon.

The balloon catheter of the invention provides for improved focal expansion and stenting due to the tapered sections proximal and distal to the working length of the balloon. Moreover, in the embodiment having the retention sections, stent migration on the balloon and the potential for damage to the vessel wall is minimized. These and other advantages of the invention will become more apparent from the following detailed description of the invention and the accompanying exemplary drawings.

DETAILED DESCRIPTION OF THE INVENTION

Figure 1:
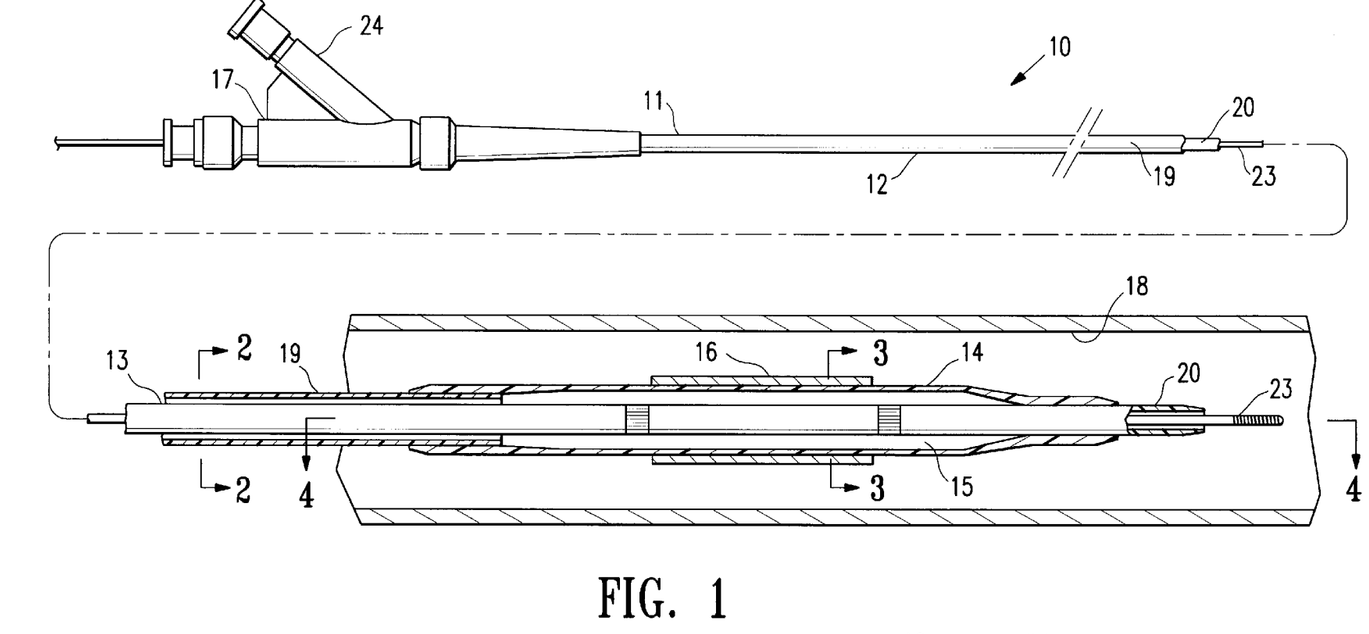
FIG. 1 is an elevational view partially in section of the catheter system which embodies features of the invention showing the balloon in an unexpanded state.
Figure 2:
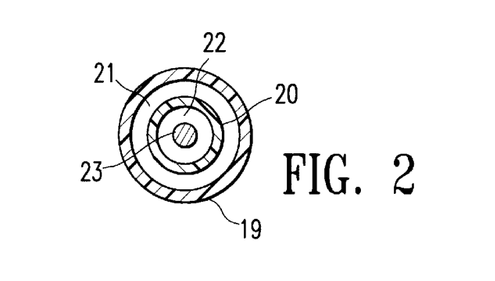
FIG. 2 is a transverse cross sectional view of the catheter system of FIG. 1 taken along lines 2—2.
Figure 3:
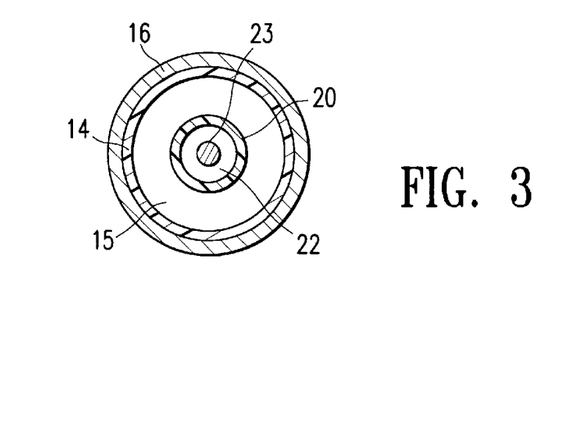
FIG. 3 is a transverse cross sectional view of the catheter system of FIG. 1 taken along lines 3—3.

FIG. 1 illustrates a balloon catheter which embodies features of the invention. The balloon catheter 10 of the invention generally includes an elongated catheter shaft 11 having a proximal section 12 and a distal 13 section, an inflatable balloon 14 on the distal section 13 of the catheter shaft 11, and an adapter 17 mounted on the proximal section 12 of shaft 11. In the embodiment illustrated in FIG. 1, the balloon catheter has a stent 16 mounted on the balloon 14, to form a stent deploying catheter system. In FIG. 1, the catheter system is illustrated within a patient's body lumen 18 prior to expansion of the balloon 14, with the balloon and stent 16 in a low profile, unexpanded state for advancement within the patient. FIGS. 2 and 3 illustrate transverse cross sectional view of the catheter shown in FIG. 1, taken along lines 2—2 and 3—3, respectively.

In the embodiment illustrated in FIG. 1, the catheter shaft 11 has an outer tubular member 19 and an inner tubular member 20 disposed within the outer tubular member and defining, with the outer tubular member, inflation lumen 21. Inflation lumen 21 is in fluid communication with the interior chamber 15 of the inflatable balloon 14. The inner tubular member 20 has an inner lumen 22 extending therein which is configured to slidably receive. a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19.

Figure 4:
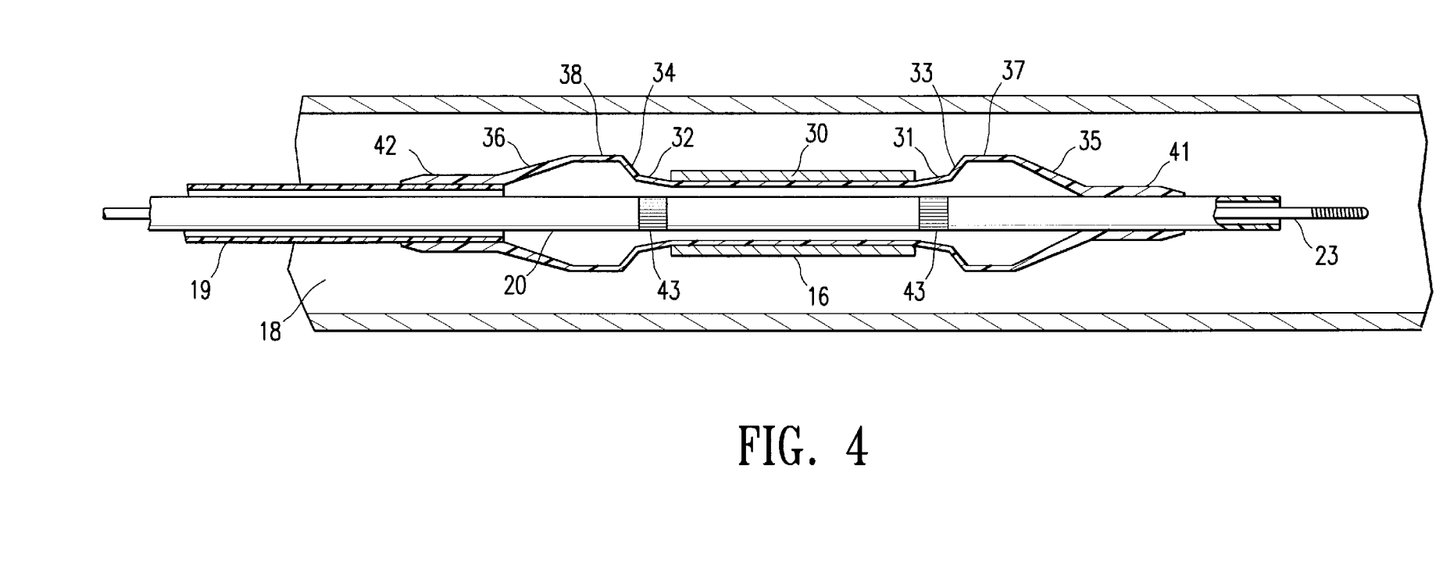
FIG. 4 is an elevational view partially in section of the distal section of a catheter system shown in FIG. 1, depicting the balloon partially expanded.
Figure 5:
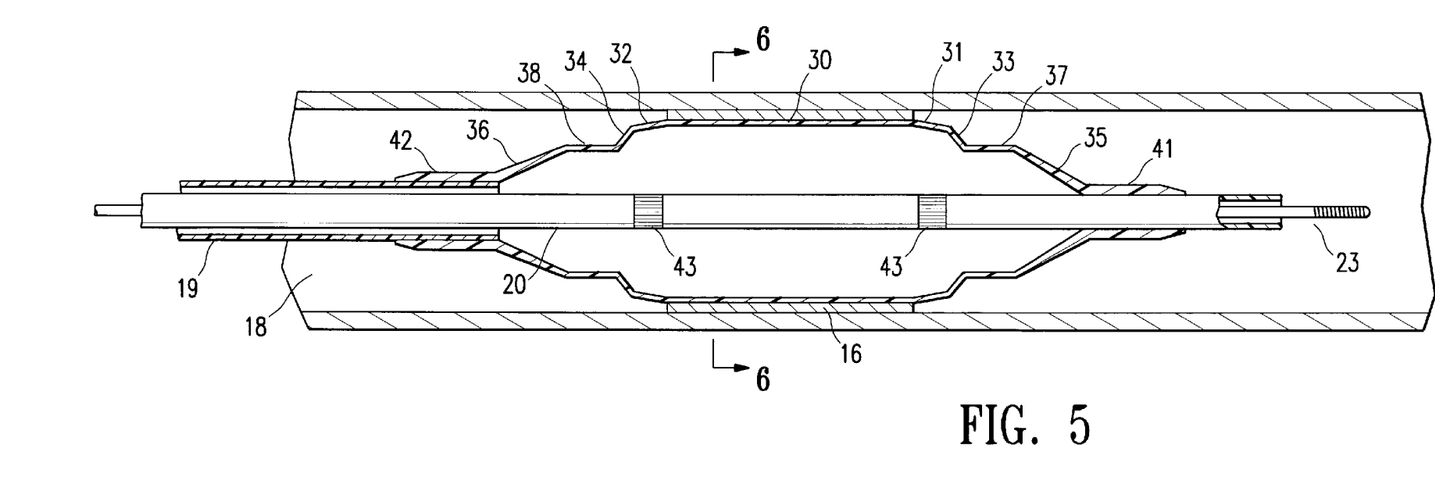
FIG. 5 is an elevational view partially in section of the distal section of the catheter system shown in FIG. 1, depicting the balloon and stent expanded.
Figure 6:
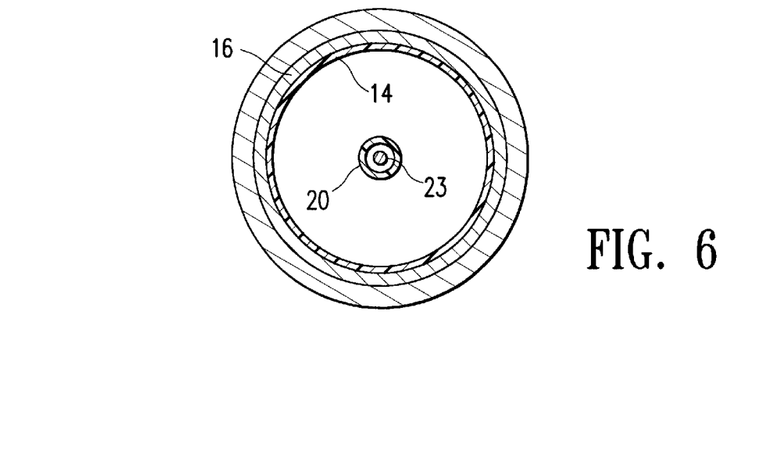
FIG. 6 is a transverse cross sectional view of the expanded balloon and stent of FIG. 5 taken along lines 6—6.

In the embodiment illustrated in FIG. 1, as best illustrated in FIG. 4 showing the balloon 14 partially inflated at low pressure less than the working pressure range of the balloon, and FIG. 5 showing the balloon inflated within the deployment pressure range, the balloon has a first section 30 centrally located on the balloon, a first tapered section 31 adjacent the distal end of the first section 30, a second tapered section 32 adjacent the proximal end of the first section. A third tapered section 33 is adjacent a distal end of the first tapered section, and a fourth tapered section 34 is adjacent a proximal end of the second tapered section. The balloon includes a fifth tapered section 35 distal to the third tapered section 33 which tapers down to a distal balloon shaft section 41, and a sixth tapered section 36 proximal to the fourth tapered section 34 which tapers down to a proximal balloon shaft section 42. The distal balloon shaft section 41 is secured to the inner tubular member, and the proximal balloon shaft section 42 is secured to the outer tubular member, using a variety of suitable means such as adhesive and fusion bonding.

In the embodiment illustrated in FIGS. 4 and 5 the balloon has a first retention section 37 adjacent to the distal end of the third tapered section 33, and a second retention section 38 adjacent to the proximal end of the fourth tapered section 34. FIG. 4 illustrates the balloon partially expanded at a first pressure less than the deployment pressure of the balloon. The first pressure is the pressure required to expand the retention sections 37, 38, which expand prior to the first section 30 when a stent is mounted on the first section 30. As illustrated in FIG. 4, at the first pressure, the first section 30 is still in a deflated low profile configuration prior to being expanded. The first and second retention sections 37, 38 expand together at the first pressure to an inflated outer diameter which is greater than the uninflated outer diameter of first section 30 and stent 16 thereon. As best illustrated in FIG. 5, when the inflation pressure is increased to the deployment pressure of the balloon, the first section 30 expands against the vessel wall to expand the stent thereon or to dilate a stenosis. The working or second pressure is the pressure required to fully inflate the balloon, and expand the first section 30 at least to the fully inflated outer diameter. The expanded outer diameter of the first and second retention sections 37, 38, inflated within the deployment range of the balloon as illustrated in FIG. 5, is less than an inner diameter of the body lumen. The first and second retention sections 37, 38 expanded outer diameter within the deployment range of the balloon is about 50% to about 75% of the expanded outer diameter of the first section 30. In the embodiment illustrated in FIG. 5, the longitudinal axis of the first section 30 is axially aligned with the longitudinal axis of the first and second retention sections 37, 38 and the catheter shaft.

As illustrated in the embodiment shown in FIG. 5, when the first section 30 of the balloon is expanded to deploy the stent by inflation within a deployment range of the balloon, the first and second tapered sections 31, 32 taper at a first angle and a second angle, respectively, to a smaller outer diameter than the inflated first section 30, and the third and fourth tapered sections 33, 34 taper at a third angle and a fourth angle, respectively, greater than the first and second angles to a smaller outer diameter than the inflated outer diameter of the first and second tapered sections. In the embodiment illustrated in FIG. 5, the first and second angles are substantially equal, and the second and third angles are substantially equal. However, in alternative embodiments the second angle may be greater or less than the first angle, and the fourth angle may be greater or less than the third angle. The first and second tapered sections 31, 32 expand to an outer diameter within the deployment pressure which is not significantly less than the expanded outer diameter of the working length. The outer diameter of the distal end of the first tapered section and the proximal end of the second tapered section (i.e., a minimum outer diameter of the first and second tapered portions) is about 85% to about 95%, preferably about 60% to about 70%, of the outer diameter of the expanded first section 30.

The first and second tapered sections 31, 32 taper at an angle of about 5° to about 25°, preferably about 10° to about 20°. The third and fourth tapered sections 33, 34 taper at an angle of about 30° to about 60°, preferably about 40° to about 50°. The fifth and sixth tapered sections 35, 36 taper at a fifth angle and sixth angle, respectively, which typically is not greater than the third or fourth angle, and which is about 15° to about 30°, preferably about 20° to about 25°. The fifth and sixth angles may be substantially equal or may be different from one another.

The stent deploying balloon of the invention can be produced by conventional techniques for producing catheter inflatable members. In a presently preferred embodiment, the balloon is formed within a mold having the general shape of the expanded balloon illustrated in FIG. 5. An extruded polymeric tube is radially expanded and axially expanded within the mold, at elevated temperatures, and may be heat treated one or more times as is conventionally known as, for example, to reduce shrinkage of the balloon. The balloon is secured to the catheter shaft, and is typically folded thereon into a low profile configuration for insertion and advancement within the body lumen of the patient.

FIG. 2, showing a transverse cross section of the catheter shaft 11, illustrates the guidewire receiving lumen 22 and inflation lumen 21. The balloon 14 can be inflated by radiopaque fluid from an inflation port 24, from inflation lumen 21 contained in the catheter shaft 11, or by other means, such as from a passageway formed between the outside of the catheter shaft and the member forming the balloon, depending on the particular design of the catheter. The details and mechanics of balloon inflation vary according to the specific design of the catheter, and are well known in the art.

The presently preferred balloon material is polyamide such as nylon 12. However, other suitable materials may be used including polyamide copolymers such as PEBAX (polyether block amide), and polyurethanes such as PEL-LETHANE (a polyurethane copolymer). The balloon material may be crosslinked or uncrosslinked, depending upon the nature of the material and characteristics required for a particular application. The presently preferred nylon balloon material is not crosslinked. By crosslinking the balloon compliant material, the final inflated balloon size can be controlled. Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure, and thereby avoid overexpanding the stent to an undesirably large diameter.

The first section 30, tapered sections 31–36, and retention sections 37, 38 of the balloon have similar compliance. The first and second retention sections 37, 38 will inflate to the expanded outer diameter illustrated in FIG. 4 at a first pressure less than the deployment range of the balloon, and will not significantly expand as the first section 30 is expanded within the deployment range of the balloon to expand the stent. However, above a pressure required to inflate the working section 30 and expand the stent, the retention sections will continue to expand up to the burst pressure of the balloon.

The balloon has sufficient strength to withstand the inflation pressures needed to inflate the balloon and expand the stent mounted thereon. The rated burst pressure of the balloon (about 3.0 mm) is about 16 atmospheres (atm), and the tensile strength of an American Standard Testing Method (ASTM) "dog-bone" sample cut from a compression molded sheet of material is about 7600 psi. The hoop strength, e.g. the product of the burst pressure and the balloon diameter, divided by two times the balloon wall thickness, of a 3.0 mm balloon of the invention is about 20,000 psi to about 40,000 psi. The first section 30 of the balloon expands to the inflated outer diameter at a deployment or second pressure of about 4 to about 10 atm, more preferably at about 6 to about 9 atm, to dilate a stenosis or expand the stent. The first and second retention sections 37, 38 expand at a first pressure of about 1 to about 3 atm, preferably about 1 to about 2 atm, before the first section 30 having a stent thereon begins to expand.

The catheter shaft will generally have the dimensions of conventional dilatation or stent deploying catheters. The length of the catheter 10 may be about 90 cm to about 150 cm, and is typically about 135 cm. The outer tubular member 19 has a length of about 25 cm to about 40 cm, an outer diameter (OD) of about 0.039 in to about 0.042 in, and an inner diameter (ID) of about 0.032 in. The inner tubular member 20 has a length of about 25 cm to about 40 cm, an OD of about 0.024 in and an ID of about 0.018 in. The inner and outer tubular members may taper in the distal section to a smaller OD or ID.

The length of the compliant balloon 14 may be about 1 cm to about 6 cm, preferably about 1.5 cm to about 3.0 cm, and is typically about 2.5 cm. With the balloon folded in a low profile configuration for introduction into and advancement within a patient's vasculature, the outer diameter of the balloon catheter at the first section 30 of the balloon with a stent thereon is about 1.0 to about 1.3 mm. In an expanded state, the wall thickness is about 0.0005 in (0.012 mm) to about 0.0025 in (0.06 mm). The balloon may be provided in a variety of sizes. The inflated outer diameter of the balloon first section 30 within the deployment pressure is about 2 to about 6 mm. The inflated outer diameter of the retention sections 37, 38 within the deployment pressure is about 1 to about 4.5 mm, preferably about 1.5 to about 4 mm. When the balloon has a stent 16 mounted thereon, the outer diameter of the retention sections at the first pressure, less than the deployment pressure, is about 1 to about 4 mm, preferably about 0.8 to about 4 mm. For example, in one embodiment, the inflated outer diameter of the balloon first section 30 within the deployment range is about 4.0 mm, and the inflated outer diameter of the balloon retention sections 37, 38 is about 2.75 mm. In a presently preferred embodiment, the length of the first section 30 is about 5 to about 60 mm. The length of the first and second tapered sections 31, 32 is about 0.1 to about 1.5 mm, and the length of the third and fourth tapered sections 33, 34 is about 0.1 to about 1.5 mm. The length of the first and second retention sections 37, and 38 is about 0.5 to about 2.5 mm. The length of the fifth and sixth tapered sections is about 0.5, to about 3 mm. In one embodiment, the balloon 14 is formed from an extruded tube having a uniform wall thickness, expanded within a mold having the desired shape. As a result, as illustrated in FIG. 5, the wall thickness of the balloon decreases as the outer diameter increases from the shaft sections 41, 42 up to the first section 30.

In the embodiment illustrated in FIGS. 4 and 5, the balloon is symmetrical and the first section 30 is at a central location on the balloon. However, alternative balloon designs may be used for particular applications and anatomies.

Various designs for dilatation catheters well known in the art may be used in the catheter system of the invention. For example, conventional over-the-wire dilatation catheters for angioplasty usually include a guidewire receiving lumen extending the length of the catheter shaft from a guidewire port in the proximal end of the shaft. Rapid exchange dilatation catheters generally include a short guidewire lumen extending to the distal end of the shaft from a guidewire port located distal to the proximal end of the shaft. Radiopaque markers 43 may be provided on the catheter shaft, as for example on the inner tubular member 20 at the proximal and distal ends of the first section 30 as illustrated in FIG. 1.

When dilating a stenosis or delivering a stent into a patient, the catheter 10 is inserted into a patient's vasculature to the desired location, and inflation fluid is delivered through the inflation lumen 21 to the balloon 14 through the inflation port 24. With a stent 16 on the first section 30, the retention sections 37, 38 will expand at the first pressure to a diameter greater than the first section 30, to keep the stent in place on the balloon. The inflation pressure is increased to the second pressure within the deployment range of the balloon to completely inflate the balloon and expand the first section 30 to dilate the stenosis or expand the stent. When the inflation fluid is removed, the balloon 14 retracts, typically to a winged or lobed shape, to allow the catheter to be withdrawn, and the stent remains in place in the patient's body lumen.

The stent 16 may be any of a variety of stent materials and forms designed to be implanted by an expanding member, such as, for example, the MULTI-LINK™ stent, commercially available from Guidant Corporation, and the stents described in U.S. Pat. No. 5,514,154 (Lau et al.) and U.S. Pat. No. 5,443,500 (Sigwart), incorporated herein by reference in their entireties. For example, the stent material may be stainless steel, a NiTi alloy, a Co—Cr—Mo containing alloy such as MP-35N, a plastic material, or various other materials. The stent has a smaller diameter for insertion and advancement into the patient's lumen which may be formed by contracting the stent or by folding at least a portion of the stent into a wrapped configuration.

It will be apparent from the foregoing that, while particular forms of the invention have been illustrated and described, various modifications can be made without departing from the spirit and scope of the invention. For example, while the balloon catheter illustrated in FIG. 1 has inner and outer tubular members with independent lumens, a single tubular membered shaft having two lumens therein may also be used. Other modifications may be made without departing from the scope of the invention.

What is claimed is:

1. A balloon catheter, comprising:
 a) an elongated shaft having a proximal end, a distal end, and an inflation lumen extending within at least a section thereof; and
 b) a balloon mounted on a distal shaft section having an interior in fluid communication with the inflation lumen, and
  a first section with an inflated outer diameter, a proximal end, and a distal end, and having a length;
  a first tapered section adjacent the distal end of the first section, tapering at a first angle to an inflated outer diameter smaller than the diameter of the first section, and having a length which is not greater than about 30% of the length of the first section of the balloon;
  a second tapered section adjacent the proximal end of the first section, tapering at a second angle to an inflated outer diameter smaller than the diameter of the first section, and having a length which is not greater than about 30% of the length of the first section of the balloon;
  a third tapered section adjacent the first tapered section, tapering at a third angle greater than the first angle to an inflated outer diameter smaller than the diameter of the first tapered section; and
  a fourth tapered section adjacent the second tapered section, tapering at a fourth angle greater than the second angle to an inflated outer diameter smaller than the diameter of the second tapered section.

2. The balloon catheter of claim 1 wherein the balloon further includes a fifth tapered section distal to the third tapered section tapering at a fifth angle to an inflated outer diameter smaller than the diameter of the third tapered section, and a sixth tapered section proximal to the fourth tapered section tapering at a sixth angle to an inflated outer diameter smaller than the diameter of the fourth tapered section.

3. The balloon catheter of claim 1 wherein the fifth angle and the sixth angle are not greater than the third angle and the fourth angle.

4. The balloon catheter of claim 1 wherein the first angle is equal to the second angle.

5. The balloon catheter of claim 1 wherein the third angle is equal to the fourth angle.

6. The balloon catheter of claim 1 wherein the first angle and the second angle are about 50 to about 25°.

7. The balloon catheter of claim 1 wherein the third angle and the fourth angle are about 30° to about 60°.

8. The balloon catheter of claim 1 wherein the fifth angle and the sixth angle are about 15° to about 30°.

9. The balloon catheter of claim 1 wherein the diameter of a distal end of the first tapered section and a proximal end of the second tapered section is about 85% to about 95% of the diameter of the first section.

10. The balloon catheter of claim 1 wherein the first section has a length of about 5 to about 60 mm.

11. The balloon catheter of claim 1 wherein the first tapered section and the second tapered section each have a length of about 0.1 to about 1.5 mm.

12. The balloon catheter of claim 1 wherein the third tapered section and the fourth tapered section each have a length of about 0.1 to about 1.5 mm.

13. The balloon catheter of claim 1 wherein the balloon further includes a first retention section between the third tapered section and the fifth tapered section, with an inflated outer diameter less than the diameter of the third tapered section, and a second retention section between the fourth tapered section and the sixth tapered section, with an inflated outer diameter less than the diameter of the fourth tapered section.

14. The balloon catheter of claim 13 wherein the inflated outer diameter of the first retention section and the second retention section is about 50% to about 75% of the inflated outer diameter of the first section.

15. The balloon catheter of claim 13 wherein the first retention and the second retention section each have a length of about 0.5 to about 2.5 mm.

16. The balloon catheter of claim 13 wherein the first section has a longitudinal axis aligned with a longitudinal axis of the first and second retention sections.

17. The balloon catheter of claim 1 wherein first section has a longitudinal axis aligned with a longitudinal axis of the catheter shaft distal section.

18. The balloon catheter of claim 13 wherein the first section and the first and second retention sections have substantially equal compliance.

19. The balloon catheter of claim 1 wherein the outer diameters are unrestrained inflated outer diameters.

20. The balloon catheter of claim 1 including an expandable stent disposed about and mounted onto the first section of the balloon so that radial expansion of the first section expands the stent.

21. The balloon catheter of claim 1 wherein the shaft comprises an outer tubular member having a guidewire lumen therein, and an inner tubular member extending in at least a portion of the outer tubular member, and wherein the inflation lumen extends between the inner and outer tubular members to a location spaced proximally of the distal end of the catheter shaft.

22. A catheter system for implanting a stent in a patient's body lumen, comprising:
   a) a balloon catheter having an elongated shaft with a proximal end, a distal end, and an inflation lumen extending within at least a section thereof;
   b) a balloon on a distal shaft section, having an interior chamber in fluid communication with the inflation lumen, and having
      a first section having a distal end, a proximal end, a first outer diameter at a first pressure, a second outer diameter greater than the first outer diameter at a second pressure greater than the first pressure;
      a first inflatable retention section distal to the distal end of the first section, and a second inflatable retention section proximal to the proximal end of the first section, the first and second retention sections each having a first outer diameter at the first pressure, and a second outer diameter at the second pressure which is less than the second outer diameter of the first section; and
   c) an expandable stent disposed about and mounted onto at least a portion of the first section of the balloon so that at least a portion of the first and second retention sections expand to the first outer diameter thereof at the first pressure which is greater than the first outer diameter of the portion of the first section of the balloon having the stent thereon, and so that inflation of the balloon at the second pressure expands the stent mounted thereon.

23. The catheter system of claim 22 wherein the second outer diameter of the first and second retention sections is about 50% to about 75% of the second outer diameter of the first section.

24. The catheter system of claim 22 wherein the second outer diameter of the first and second retention sections is about 60% to about 70% of the second outer diameter of the first section.

25. The catheter system of claim 22 wherein the second outer diameter of the first and second retention sections is less than an inner diameter of the body lumen.

26. The catheter system of claim 22 wherein a distal end of the stent is proximal to the first retention section, and a proximal end of the stent is distal to the second retention section.

27. The catheter system of claim 22 wherein the first pressure is about 1 to about 3 atmospheres.

28. The catheter system of claim 22 wherein the second pressure is about 6 to about 10 atmospheres.

29. The catheter system of claim 22 wherein the balloon is formed of a polymeric material selected from the group consisting of polyamide, polyether block amide, and polyurethane, and at least the first section of the balloon has a low compliance.

30. The catheter system of claim 22 wherein the compliance of the first section is substantially equal to the compliance of the first and second retention sections.

31. The catheter system of claim 22 further including a first tapered section adjacent the distal end of the first section tapering at a first angle, and a second tapered section adjacent the proximal end of the first section tapering at a second angle, and a third tapered section between the first tapered section and the first retention section tapering at a third angle greater than the first angle, and a fourth tapered section between the second tapered section and the second retention section tapering at a third angle greater than the second angle.

32. A catheter system for implanting a stent in a patient's body, comprising:
   a) a catheter having an elongated shaft with proximal and distal ends and an inflation lumen extending within at least a portion of the shaft to a location spaced proximally from a distal end of the catheter;
   b) a balloon mounted on a distal shaft section having an interior in fluid communication with the inflation lumen, and
      a first section with an inflated outer diameter, a proximal end, and a distal end;
      a first tapered section adjacent the distal end of the first section with an inflated outer diameter smaller than the diameter of the first section, and tapering at a first angle;
      a second tapered section adjacent the proximal end of the first section with an inflated outer diameter smaller than the diameter of the first section, and tapering at a second angle;
      a third tapered section adjacent the first tapered section with an inflated outer diameter smaller than the diameter of the first tapered section, and tapering at a third angle greater than the first angle; and
      a fourth tapered section adjacent the second tapered section with an inflated outer diameter smaller than the diameter of the second tapered section, and tapering at a fourth angle greater than the second angle; and
   c) an expandable stent disposed about and mounted onto at least a portion of the balloon so that radial expansion of the balloon to the inflated diameter expands the stent mounted thereon.

33. The catheter system of claim 32 wherein the first angle and the second angle are about 5° to about 25°.

34. The catheter system of claim 32 wherein the third angle and the fourth angle are about 30° to about 60°.

35. The catheter system of claim 32 wherein the first tapered section and the second tapered section have a minimum outer diameter which is about 85% to about 95% of the inflated outer diameter of the first section.

36. The catheter system of claim 32 wherein the third and fourth tapered sections have a minimum outer diameter which is about 60% to about 70% of the inflated outer diameter of the first section.

37. A method of implanting a stent within a patient's body, comprising:
a) providing a catheter system for implanting a stent in a patients body, comprising:
  i) a catheter having an elongated shaft with proximal and distal ends and an inflation lumen extending within at least a distal shaft section to a location spaced proximally from the distal end;
  ii) a balloon mounted on the distal section of the catheter shaft with an interior chamber in fluid communication with the inflation lumen, having
    a first section with an inflated outer diameter, a proximal end, and a distal end;
    a first tapered section adjacent the distal end of the first section with an inflated outer diameter smaller than the diameter of the first section, and tapering at a first angle;
    a second tapered section adjacent the proximal end of the first section smaller than the diameter of the first section, and tapering at a second angle;
    a third tapered section adjacent the first tapered section with an inflated outer diameter smaller than the diameter of the first tapered section, and tapering at a third angle greater than the first angle; and
    a fourth tapered section adjacent the second tapered section with an inflated outer diameter smaller than the diameter of the second tapered section, and tapering at a fourth angle greater than the second angle; and
  iii) an expandable stent disposed about and mounted onto at least the first section of the balloon so that inflation of the first section of the balloon expands the stent mounted thereon and implants the stent in the body;
b) inserting the catheter system into the patient's body; and
c) inflating the balloon to produce radial expansion of the balloon and the stent mounted thereon, and implant the stent in the patient.

38. The method of claim 37 wherein the stent distal end is distal to the distal end of the first section, and step c includes expanding the distal end of the stent by inflating the first tapered section.

39. The method of claim 37 wherein the stent proximal end is proximal to the proximal end of the first section, and c includes expanding the proximal end of the stent by inflating the second tapered section.

40. The method of claim 37 wherein the balloon has a first retention section and a second retention section, each retention section having
a) a first outer diameter at a first pressure lower than a deployment range of the balloon, the first outer diameter of the first and second retention sections being greater than a first outer diameter of the first section at the first pressure; and
b) a second outer diameter at a second pressure greater than the first pressure which is about 50% to about 75% of the inflated outer diameter of the first section within the deployment range, and including expanding the first and second retention sections at the first pressure to inhibit longitudinal displacement of the stent during inflation of the balloon.

41. The method of claim 37 further including inflating the balloon by delivering inflation fluid through the inflation lumen to the balloon interior chamber.

42. A balloon catheter, comprising:
a) an elongated shaft with a proximal end, a distal end, and an inflation lumen extending within at least a section thereof; and
b) a balloon on a distal shaft section, having an interior chamber in fluid communication with the inflation lumen, and having
  a first inflatable section having a distal end, a proximal end, a first outer diameter at a first pressure, a second outer diameter greater than the first outer diameter at a second pressure greater than the first pressure;
  a first inflatable tapered section adjacent the distal end of the first section tapering at a first angle;
  a second inflatable tapered section adjacent the proximal end of the first section tapering at a second angle;
  a first inflatable intermediate section distal to the distal end of the first section, and a second inflatable intermediate section proximal to the proximal end of the first section, the first and second intermediate sections each having a first outer diameter at the first pressure, and a second outer diameter at the second pressure which is less than the second outer diameter of the first section;
  a third inflatable tapered section between the first tapered section and the first intermediate section tapering at a third angle greater than the first angle;
  a fourth inflatable tapered section between the second tapered section and the second intermediate section tapering at a fourth angle greater than the second angle; and
  a distal balloon shaft section distal to the first intermediate section and secured to the catheter shaft, and a proximal balloon shaft section proximal to the second intermediate section and secured to the catheter shaft.

43. The balloon catheter of claim 42 including an expandable stent disposed about and mounted onto at least a portion of the first section of the balloon so that inflation of the balloon at the second pressure expands the stent mounted thereon.

44. The balloon catheter of claim 43 wherein the balloon further includes a fifth inflatable tapered section between the first intermediate section and the distal balloon shaft section with an inflated outer diameter smaller than the diameter of the third tapered section, and a sixth inflatable tapered section between the second intermediate section and the proximal balloon shaft section with an inflated outer diameter smaller than the diameter of the fourth tapered section.

45. A balloon catheter, comprising:
a) an elongated shaft having a proximal end, a distal end, and an inflation lumen extending within at least a section thereof; and
b) a balloon mounted on a distal shaft section having an interior in fluid communication with the inflation lumen, and
  a first section with an inflated outer diameter, a proximal end, and a distal end;
  a first tapered section adjacent the distal end of the first section tapering at a first angle to an inflated outer diameter smaller than the diameter of the first section;

a second tapered section adjacent the proximal end of the first section tapering at a second angle to an inflated outer diameter smaller than the diameter of the first section;

a third tapered section adjacent the first tapered section tapering at a third angle greater than the first angle to an inflated outer diameter smaller than the diameter of the first tapered section;

a fourth tapered section adjacent the second tapered section tapering at a fourth angle greater than the second angle to an inflated outer diameter smaller than the diameter of the second tapered section;

a fifth tapered section distal to the third tapered section tapering to an inflated outer diameter smaller than the diameter of the third tapered section; and a sixth tapered section proximal to the fourth tapered section tapering to an inflated outer diameter smaller than the diameter of the fourth tapered section.

* * * * *

UNITED STATES PATENT AND TRADEMARK OFFICE
CERTIFICATE OF CORRECTION

PATENT NO.    : 6,383,212 B2
DATED         : May 7, 2002
INVENTOR(S)   : Jonathan P. Durcan et al.

It is certified that error appears in the above-identified patent and that said Letters Patent is hereby corrected as shown below:

<u>Column 8,</u>
Line 49, change "50", to read -- $5^0$ --.

Signed and Sealed this

Tenth Day of September, 2002

Attest:

JAMES E. ROGAN
Attesting Officer    Director of the United States Patent and Trademark Office